(12) United States Patent
Aebi et al.

(10) Patent No.: US 11,395,687 B2
(45) Date of Patent: Jul. 26, 2022

(54) INSERTION TOOL FOR FLIP ANCHOR CABLE SYSTEM INSERTION

(71) Applicant: DEPUY SYNTHES PRODUCTS, INC., Raynham, MA (US)

(72) Inventors: This Aebi, Zuchwil (CH); Daniel Andermatt, Zuchwil (CH); Mirko Rocci, Bettlach (CH); Eric Liu, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 817 days.

(21) Appl. No.: 16/290,086

(22) Filed: Mar. 1, 2019

(65) Prior Publication Data

US 2020/0275920 A1 Sep. 3, 2020

(51) Int. Cl.
*A61B 17/88* (2006.01)
*A61B 17/84* (2006.01)
(Continued)

(52) U.S. Cl.
CPC ...... *A61B 17/8861* (2013.01); *A61B 17/0401* (2013.01); *A61B 17/683* (2013.01); *A61B 17/842* (2013.01); *A61B 17/8872* (2013.01); *A61B 2017/0023* (2013.01); *A61B 2017/00429* (2013.01); *A61B 2017/00845* (2013.01); *A61B 2017/00853* (2013.01); *A61B 2017/0409* (2013.01); *A61B 2017/681* (2013.01); *A61B 2090/034* (2016.02); *A61B 2090/0807* (2016.02); *A61F 2002/0852* (2013.01)

(58) Field of Classification Search
None
See application file for complete search history.

(56) References Cited

U.S. PATENT DOCUMENTS 5,329,846 A 7/1994 Bonutti
5,662,658 A 9/1997 Wenstrom, Jr.
(Continued)

FOREIGN PATENT DOCUMENTS

EP 2 626 014 A2 8/2013
WO 97/25928 A1 7/1997

*Primary Examiner* — Tessa M Matthews
(74) *Attorney, Agent, or Firm* — Kramer & Amado, P.C.

(57) ABSTRACT

A tool useful for deploying a flip anchor connected to a cable includes a housing with a first end and a second end; and a guiding tube having a bore therethrough. The guiding tube has a proximal end releasably connected to the first end of said housing, and a distal end configured to hold said flip anchor. The housing includes a mechanism having a low resistance surface and a slider having a high friction surface facing the low resistance surface, where the slider is movable between a) a clamping position configured to clamp the cable between the low resistance surface and the high friction surface; and b) a release position configured to allow the cable to move freely on the low resistance surface. A safety button on said housing is movable between an elevated position where the safety button holds the slider in said first position, and a depressed position where the safety button releases the slider, allowing it to enter the second position. The slider is configured to move the cable distally upon movement from the clamping position to the release position, deploying the flip anchor from the guiding tube.

21 Claims, 5 Drawing Sheets

(51) Int. Cl.
   *A61B 17/68*   (2006.01)
   *A61B 90/00*   (2016.01)
   *A61B 17/00*   (2006.01)
   *A61B 17/04*   (2006.01)
   *A61F 2/08*    (2006.01)

(56) References Cited

U.S. PATENT DOCUMENTS

| | | |
|---|---|---|
| 5,788,697 A | 8/1998 | Kilpela et al. |
| 5,814,051 A | 9/1998 | Wenstrom, Jr. |
| 5,860,983 A | 1/1999 | Wenstrom, Jr. |
| 5,994,724 A | 11/1999 | Morikawa |
| 6,068,648 A | 5/2000 | Cole et al. |
| 6,544,267 B1 | 4/2003 | Cole et al. |
| 6,761,722 B2 | 7/2004 | Cole et al. |
| 7,153,312 B1 | 12/2006 | Torrie et al. |
| 7,713,283 B2 | 5/2010 | Forsberg |
| 8,641,717 B2 | 2/2014 | Defossez et al. |
| 8,795,298 B2 | 8/2014 | Hernlund et al. |
| 9,173,647 B2 * | 11/2015 | Bonutti ................ A61B 17/842 |
| 9,848,859 B2 | 12/2017 | White |
| 2002/0188301 A1 | 12/2002 | Dallara et al. |
| 2006/0190042 A1 | 8/2006 | Stone et al. |
| 2015/0045795 A1 * | 2/2015 | Sholev ............... A61B 17/1604 |
| | | 606/79 |
| 2015/0297213 A1 | 10/2015 | Lehtinen et al. |
| 2015/0342657 A1 * | 12/2015 | Voisard ................ A61B 17/823 |
| | | 606/103 |
| 2017/0325867 A1 | 11/2017 | Rapier et al. |
| 2021/0128214 A1 * | 5/2021 | Esser ................ A61B 17/8861 |

\* cited by examiner

INSERTION TOOL FOR FLIP ANCHOR CABLE SYSTEM INSERTION

TECHNICAL FIELD

Various exemplary embodiments disclosed herein relate generally to an insertion tool for inserting a flip anchor cable.

BACKGROUND

It is a common requirement in orthopedic surgical procedures to anchor two or more elements together, such as pieces of a bone, two or more bones, or a combination of soft tissue and bone. This has been accomplished by a number of devices, such as bone bolts that penetrate two pieces of bone and use a nut to draw the segments together, bone screws and interconnecting plates, wires circling at least two pieces of bone, or sutures into the tissue.

Often such devices require a relatively large access opening through surrounding and/or covering tissue to implant the anchoring devices. The enlarged access site may increase patient pain and lengthen recovery time. Further, in some locations it is difficult and impractical to make large access points to reach the appropriate site because of surrounding joints and vessels. Even with devices that penetrate the tissue in a substantially linear manner, i.e., lag bolts, the fracture must often be reduced before drilling and insertion of the bolt. Further, some of these devices may be difficult to use since it may be hard to reduce a fracture between two bone segments and maintain that reduction while the device is inserted. This is particularly true with small bone fragments where the use of threaded implants may tend to rotate one bone segment with respect to another, thereby creating a misalignment between the fragments.

Cerclage systems provide an alternative to implants that must penetrate the bone to achieve fixation. These systems rely on passing a cable around two segments of bone and then tensioning the cable to squeeze the bone segments together. A significant drawback of these systems is that they require access around the entire bone.

A flip anchor cable system provides a convenient and effective system for securing two segments of tissue together. Such a system may be operable through a relatively small insertion opening or openings to securely hold two tissue segments. Such a cable system may be inserted through openings in two bones or other tissues to be anchored together. To maintain proper alignment, a guiding tube may be inserted through the openings in the tissue segments, with the flip anchor cable being positioned in the guiding tube. Once the flip anchor is in position, the guiding tube is removed, and the cable is pulled taught.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments disclosed herein relate to a system for use in deploying a flip anchor cable, where said flip anchor cable includes a flip anchor, and a cable connected to the flip anchor ("flip anchor cable"). The system may include a housing having a first end and a second end; and a guiding tube having a first axis and a bore therethrough, where the guiding tube has a proximal end releasably connected to the first end of said housing and a distal end. The distal end of the guiding tube is configured to hold the flip anchor, so that a first portion of the flip anchor cable extends through the guiding tube and a second portion of the flip anchor cable is stored within the housing. In various embodiments, the guiding tube is removed from the housing and discarded after a single use, or after use on a single patient. The housing may be sterilized after use on a first patient, and reused on a different patient.

In various embodiments, the housing includes a mechanism having a low resistance surface and a slider mounted on the housing. The slider includes a high friction surface facing the low resistance surface, with the slider being movable between
  a clamping position configured to clamp the second portion of the flip anchor cable between said low resistance surface and said high friction surface; and
  a release position configured to allow the cable to move freely on said low resistance surface.

In various embodiments, the low resistance surface may be a low friction surface. Suitable low friction surfaces may be sheets or pads of a low friction polymer, such as polytetrafluoroethylene, polyimide, PEEK, polyphenylene sulfide, nylon, silicones, polyacetals, and polyesters. Other materials having a low friction surface, such as diamond-like carbon, may be used. Additional materials with suitable frictional properties are known in the art. In various embodiments, the low resistance surface may be a roller, or a set of two or more rollers. Such a roller is not required to have a low friction surface, as long as the roller rotates freely as the flip anchor cable travels on the roller surface.

In various embodiments, the housing includes a safety button, the safety button being movable between an elevated position and a depressed position. When the safety button is elevated, the button engages the slider and holds it in the clamping position. When the safety button is depressed, the safety button disengages the slider, allowing it to enter the release position. In various embodiments, the slider is configured to drive the flip anchor cable distally along the guiding tube upon movement from said clamping position to said release position, deploying the flip anchor from the guiding tube at the desired site for securing bones or other tissues together. After deployment of the flip anchor, the g tiding tube and housing of the flip anchor deployment system are withdrawn, leaving the flip anchor and cable in place. The cable is then pulled taught to secure the tissues together. After withdrawal of the guiding tube and housing, the guiding tube may be separated from the housing and discarded, while the housing may be sterilized for reuse.

In various embodiments, the low resistance surface in the housing includes a low friction plastic, such as a silicone or a fluorinated polymer, e.g., polytetrafluoroethylene. In some embodiments, the low resistance surface includes at least one roller, and may include one, two, three, or more rollers. In various embodiments, the high friction surface on the slider is a toothed surface, an etched surface, a sandblasted surface, or a surface coated with a layer of an aggregate and a binder.

In various embodiments disclosed herein, the housing includes a safety button movable between an elevated position and a depressed position, where the safety button is biased toward the elevated position, but may be releasably locked into said position. The housing also includes a mechanism having a slider mounted on the housing, with the slider being movable between a clamping position configured to clamp the flip anchor cable between a low resistance surface in the housing and a high friction surface on the slider; and a release position configured to allow the cable to move freely on said low resistance surface. The slider is biased toward the safety button, and engages the safety button when the safety button is in its elevated position, but does not engage the safety, button when the safety button is in its depressed position.

In various embodiments, the proximal end of the guiding tube fits into an opening in the housing. In some embodiments, the proximal end of the guiding tube has a male end with a noncircular cross section which fits into a female opening in said housing, where the female opening has a corresponding noncircular cross section. In various embodiments, the proximal end of the guiding tube and the opening in the housing may each have a D-shaped cross section with a single planar surface. In various embodiments, the proximal end of the guiding tube and the opening in the housing may each have a teardrop-shaped cross section with two intersecting planar surfaces. In some embodiments, the proximal end of the guiding tube has a male end with a threaded surface which fits into the opening in said housing, where the opening in the housing has an inner surface with a corresponding female thread. In some embodiments, the proximal end of the guiding tube has tabs on an outer surface, said tabs screwing into a sleeve with a threaded inner surface, where the sleeve surrounds the opening in the housing. In certain embodiments, the guiding tube and housing are assembled by a snap-fit mechanism, where the proximal end of the guiding tube has a ridge, and the opening in said housing has a groove. In such embodiments, the ridge may snap into the groove so as to releasably engage the groove.

In various embodiments, the proximal end of the guiding tube includes a washer which engages the opening in a first end of the housing. The second end of the housing includes a hinge which allows the housing to be divided into a first half having an upper portion of said opening, and a second half having a lower portion of said opening, where the upper and lower portions of the opening each include a washer-engaging surface. The washer-engaging surfaces in the upper and lower portions of the opening are configured to lock the washer of the guiding tube to said housing when the hinge is closed, and release the washer when the hinge is open.

Various embodiments disclosed herein relate to a system for use in deploying a flip anchor cable, wherein said flip anchor cable includes a flip anchor and a cable connected to the flip anchor, where the system includes a housing having a first end having an opening and a second end, where the second end of the housing includes a hinge allowing the housing to be divided into a first half and a second half. A guiding tube has a first axis and a bore therethrough, with a proximal end releasably mounted in said opening in the first end of the housing, and a distal end configured to hold the flip anchor so that a first portion of the cable extends through the bore of the guiding tube. The housing stores a second portion of the cable, and includes a mechanism having a low resistance surface and a slider with a high friction surface, positioned so that the low resistance surface faces the high friction surface on the slider. The slider is movable between a) a clamping position configured to clamp the cable between the low resistance surface and said high friction surface; and b) a release position configured to allow the cable to move freely on said low resistance surface. A safety button on the housing has an elevated position where the safety button holds the slider in the clamping first position, and a depressed position where the safety button releases the slider. Pressing the safety button locks the safety button into said depressed position until said hinge is opened. When the safety button is in its depressed position, the slider may be moved from its clamping position to its release position. This motion drives the cable distally in the guiding tube, deploying the flip anchor from the guiding tube. In various embodiments, the system is configured to produce a signal, such as an audible noise, when the slider enters the release position, indicating that the flip anchor has been deployed Various embodiments disclosed herein relate to a tool for use in deploying a flip anchor cable from a guiding tube having a bore therethrough, where the flip anchor cable includes a flip anchor deployably positioned at one end of the guiding tube, and a cable connected to the flip anchor. The cable has a first portion extending through the guiding tube. The tool includes:
   a housing having a first end releasably holding tae guiding tube, and a second end; and
   a mechanism having a low resistance surface and a slider on the housing, where the slider has a high friction surface facing the low resistance surface.

The housing is configured to hold a second portion of the cable extending from the guiding tube, so that the second portion of the cable passes between the high friction surface and the low resistance surface. The slider is movable between
   a) a clamping position configured to clamp the second portion of the cable between the low resistance surface and the high friction surface; and
   b) a release position configured to allow the cable connected to the flip anchor to move freely on said low resistance surface.

In various embodiments, the tool includes a safety button on the housing. The safety button has an elevated position where the safety button holds the slider in its clamping position, and a depressed position where the safety button releases the slider, allowing it to enter the release position. The slider may be configured to drive the cable connected to the flip anchor distally along the guiding tube upon movement from said clamping position to said release position, deploying said flip anchor from said guiding tube.

Various embodiments disclosed herein relate to a system for use in deploying a flip anchor cable, including a housing, the housing having a first end having an opening and a second end, the second end of said housing including a hinge, the hinge allowing the housing to be divided into a first half and a second half. A guiding tube has a first axis and a bore therethrough, said tubular insertion tool having a proximal end, the proximal end being releasably mounted in said opening in the first end of the housing, and a distal end configured to hold the flip anchor. The housing includes a mechanism having a low resistance surface and a slider on the housing, the slider having a high friction surface facing the low resistance surface. The slider is movable between a clamping position configured to clamp the cable between the low resistance surface and the high friction surface; and a release position configured to allow the cable to move freely on said low resistance surface. A safety button on the first half of the housing moves between an elevated position where file safety button holds the slider in said clamping, position, and a depressed position where the safety button releases the slider, allowing it to enter the release position. The slider is configured to move the cable distally upon movement from said clamping position to said release position, deploying said flip anchor. The safety button engages the second half of the housing upon movement into the depressed position, locking the safety button in the depressed position until the hinge is opened. The safety button may be configured to remain in the depressed position until the hinge is closed.

In various embodiments, the guiding tube has a proximal end with an outer surface which is non-circular. The distal end of the housing has an opening configured to receive the proximal end of the guiding tube, where the opening in the housing has an inner surface with a corresponding non-circular surface. In various embodiments, the proximal end of the guiding tube may have an outer surface e with a planar portion, while the opening in the housing has an inner surface with a corresponding planar surface, so that the planar surfaces interact to prevent rotation of the guiding tube relative to the housing. The distal end of the guiding tube may also have an inner surface which is configured to prevent rotation of the flip anchor around an axis of the guiding tube. The distal end of the guiding tube may be deformed into a noncircular shape, i.e., a D-shape, an oval shape, or a rectangular shape, to prevent rotation of the flip anchor.

It is contemplated that various combinations of the embodiments described herein may be made resulting in additional embodiments that are within the scope of the invention described herein.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiment.

A flip anchor cable is described in U.S. Pat. No. 6,761,722 to Cole et al. ("Cole"), which is hereby incorporated by reference for all purposes as if fully set forth herein. The flip anchor cable may be used to anchor tissue, for example, bone, cartilage, ligaments, tendons, muscle, etc. For example, the flip anchor cable may be used to reduce and secure a bone fracture. A hole may be drilled through the bone and the cable inserted through the hole. The flip anchor cable has an anchor at the end of the cable that is aligned with the cable during insertion. Once the anchor passes through the bone, the anchor rotates so that as the cable is then pulled back through the insertion hole, and the anchor is affixed to the bone surrounding the insertion hole. As tension is applied to the cable, the fracture in the bone may be reduced and secured. The cable may then be fixed in place by placing a ferrule over the cable and crimping the ferrule in place to securely anchor the reduced fracture. Other methods of securing the cable are also discussed in Cole.

Embodiments of an insertion tool that facilitate the insertion of the flip anchor cable are described below. This insertion tool provides the following features that facilitate the insertion of the flip anchor cable.

The insertion tool provides faster insertion of the flip anchor cable resulting in a shorter insertion time. The insertion tool also provides easier handling of the flip anchor cable to reduce the attention that a user has to give to handling the insertion of the flip anchor cable. Further, the insertion tool facilitates one handed use which allows the user to use their other hand for other tasks. The insertion tool protects and covers the cable which allows the cable to remain sterile and also makes handling the flip anchor cable simpler.

Figure 1:
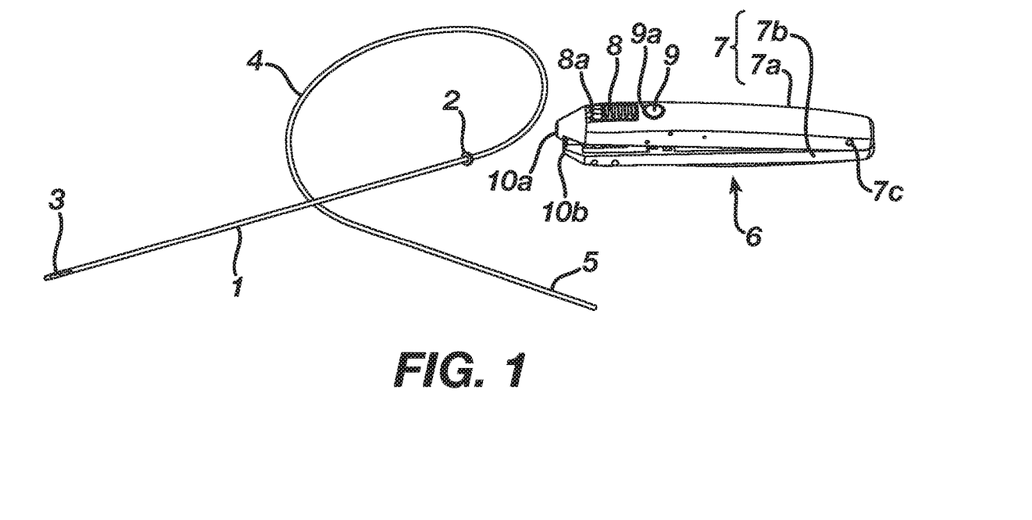
FIG. 1 provides a perspective view of the flip anchor cable insertion tool in an open state (right) and a flip anchor cable positioned in a guiding tube (left)

FIG. 1 provides a view of a flip anchor cable 4 loaded into a guiding tube 1, and a flip anchor cable insertion tool 6 in an open state, ready to receive guiding tube 1. The guiding tube 1 includes a washer, ridge, or flange 2 on a proximal end. The flip anchor cable includes a flip anchor 3 at a first cable end, and may include a rigid handle 5 at a second cable end. A first portion of the flip anchor cable is positioned in the guiding tube so that the flip anchor is positioned at the distal end of the guiding tube in a non-deployed state, while a second portion of the cable extends from the proximal end of the guiding tube.

As seen in FIG. 1, the cable insertion tool 6 includes a housing 7 defined by upper shell 7a and lower shell 7b, where the upper and lower shells are joined by hinge 7c at a proximal end of tool 6. The housing includes two jaws, jaw 10a in upper shell 7a and lower jaw 10b in lower shell 7b, where the jaws define an opening for receiving washer, ridge, or flange 2 at a distal end of the housing and secure guiding tube 1 to insertion tool 6. On the upper surface of tool 6 is a safety button 9 and a slider 8. Slider 8 is biased toward the proximal end of tool 6 by a spring 15 (shown in FIG. 5, discussed later), but may be moved distally toward the proximal end of tool 6 along slot 8a in upper shell 7a. Safety button 9 is movable from an elevated position to a depressed position in a hole 9a in upper shell 7a.

Figure 2:
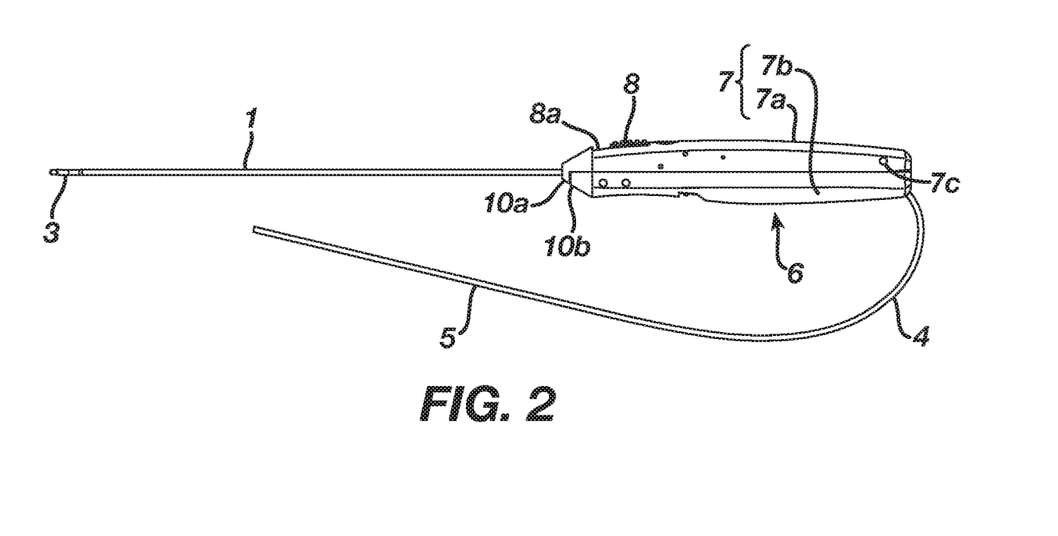
FIG. 2 illustrates an expanded view of the flip anchor cable insertion tool in a closed state, holding a guiding tube with a flip anchor cable therein.

FIG. 2 shows an assembly including the insertion tool 6, guiding tube 1, and flip anchor cable 4, where upper and lower shells 7a and 7b have been closed about hinge 7c. Jaws 10a and 10b have been closed around ridge 2 (not visible in FIG. 2), so that guiding tube 1 is secured to the distal end of the insertion tool 6. A first portion of the flip anchor cable is positioned in the guiding tube so that the flip anchor 3 is positioned at the distal end of the guiding tube 1 in a non-deployed state, while a second portion of the cable 4 passes through the housing of the insertion tool and extends from the proximal end of the housing. If desired, the free end of the second portion may be stored in a chamber in the housing of insertion tool 6.

Figure 3:
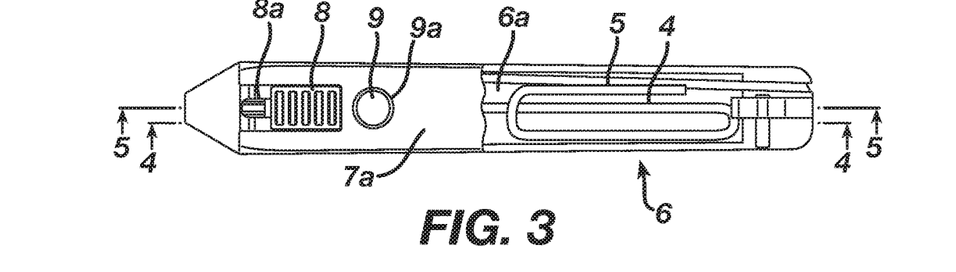
FIG. 3 illustrates a partially cut away top view of the flip anchor cable insertion tool.

FIG. 3 shows a top view of insertion tool 6, showing upper shell 7a. Safety button 9 extends through hole 9a in upper shell 7a, while slider 8 is able to slide distally and back again along slot 8a in upper shell 7a. In FIG. 3, the rear portion of shell 7a has been cut away, showing chamber 6a in the housing of insertion tool 6. As seen in FIG. 3, the free end of cable 4 may be coiled, and stored along with handle 5 in chamber 6a.

Figure 4:
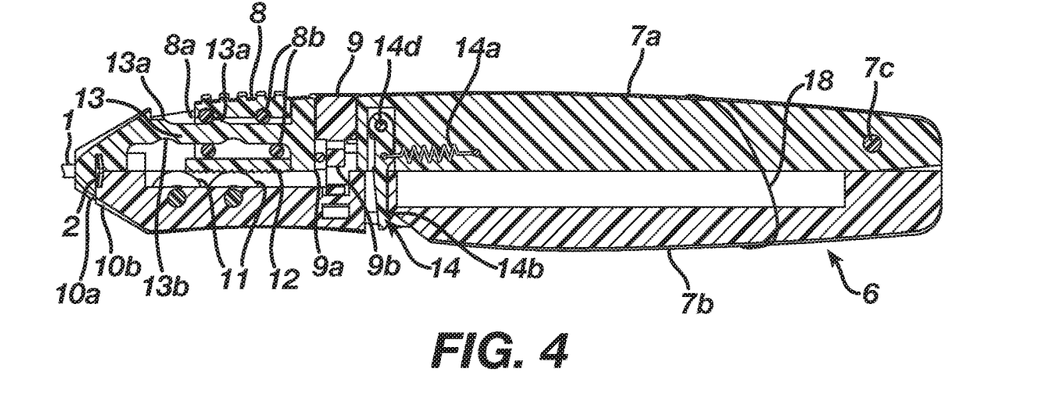
FIG. 4 shows a first cross-sectional view of the flip anchor cable insertion tool, along arrows 4 of FIG. 3.

FIG. 4 shows a cross section of the inserter tool of FIG. 3, in the direction of arrows 4 of FIG. 3. Inserter tool 6, with guiding tube 1 (not shown in FIG. 3) attached, is shown in a closed position about hinge 7c. Jaws 10a and 10b are closed about flange or ridge 2 of guiding tube 1, holding guiding tube 1 in position. Slider 8, mounted in upper shell 7a, has a high friction surface 12 on its lower surface. The high friction surface 12 may be a toothed surface, as seen in FIG. 4. The high friction surface may also be an etched surface, a sandblasted surface, or a surface coated with a layer of an aggregate and a binder. Lower shell 7b has a low resistance surface which faces the high friction surface. The low resistance surface may be made from a low friction plastic, such as a silicone or a fluoropolymer, e.g., polytetrafluoroethylene. The low resistance surface may also be at least one roller with a polymeric or metal surface. The low resistance surface may include a series of one, two, three, or more than three rollers, as seen in FIG. 4.

According to FIG. 4, slider 8 is moveable along slot 8a along two struts 13 (one on each side of slider 8; only one strut 13 is shown in FIG. 4). On each side of slider 8, four pegs 8b contact strut 13, with two pegs riding above strut 13 and two pegs riding below strut 13. On the upper surface of strut 13, two peaks 13a are situated so that the peak-to-peak distance between peaks 13a is equal to the distance between the centers of the two pegs 8b above strut 13. On the lower surface of strut 13, two troughs 13b are situated so that the peak-to-peak distance between troughs 13b is equal to the distance between the centers of the two pegs 8b below strut 13. As shown in FIG. 4, the high friction surface 12 contacts low resistance surface. As slider 8 moves distally along slot 8a, pegs 8b move along strut 13 until they reach peaks 13a and troughs 13b. Peaks 13a and troughs 13b cause pegs 8b to move upwards relative to the low resistance surface, lifting the high friction surface away from the low resistance surface.

FIG. 4 also shows button 9, which has at least one inwardly biased support 9b attached thereto. Button 9 and the associated support or supports 9b move vertically from an elevated position to a depressed position along a hole 9a in upper shell 7b.

As seen in FIG. 4, upper and lower shells 7a and 7b are releasably closed about hinge 7c by hook 14, rotatably mounted in upper shell 7a on a pin 14d. Hook 14 holds upper and lower shells 7a and 7b in a closed position by hooking over ledge 14b in lower shell 7b. Spring 14a biases hook 14 in a proximal direction over ledge 14b, toward hinge 7c, preventing accidental disengagement of shells 7a and 7b. Hook 14 may be manually pushed in a distal direction, against the proximal bias applied by spring 14a, to allow disengagement of shells 7a and 7b. At this point, spring 18, which may be a leaf spring or a coil spring, biases shells 7a and 7b from a closed position, as seen in FIG. 4, to an open position, as seen in FIG. 1. It is noted that alternatively, the hook could be flipped vertically so that it is attached to the lower shell 7b and hooks the upper shell 7a.

Figure 5:
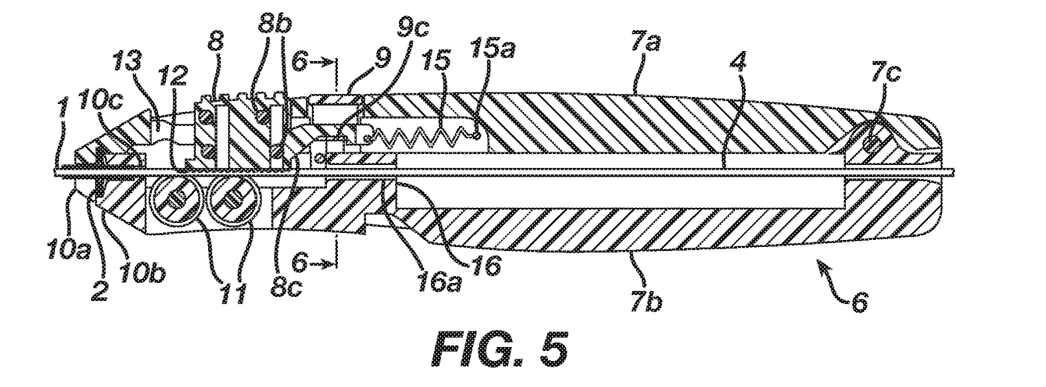
FIG. 5 shows a second cross-sectional view of the flip anchor cable insertion tool, along arrows 5 of FIG. 3.

FIG. 5 shows a cross section of the inserter tool of FIG. 3, in the direction of arrows 5 of FIG. 3. Inserter tool 6, with guiding tube 1 (not shown in FIG. 3) attached, is shown in a closed position about hinge 7c, with jaws 10a and 10b being closed about flange or ridge 2 of guiding tube 1, holding guiding tube 1 in position. A proximal end of guiding tube 1 passes through a bore or opening 10c in jaw 10b. Cable 4 passes through guiding tube 1, and along the length of the housing, with cable 4 passing between high friction surface 12 and low resistance surface 11 (a pair of rollers, in the embodiment of FIG. 5). As seen in FIG. 5, a hook-shaped extension 8c of slider 8 extends through an opening in button 9, and hooks over strut 9c at the bottom of the opening in button 9 when button 9 is in an elevated position. Interaction between extension 8c and strut 9c holds slider 8 in a first clamping position, with cable 4 being clamped between high friction surface 12 and low resistance surface 11. Spring 15 extends between the rear of extension 8c and pin 15a in upper shell 7a, biasing slider 8 toward the first clamping position.

Figure 6A:
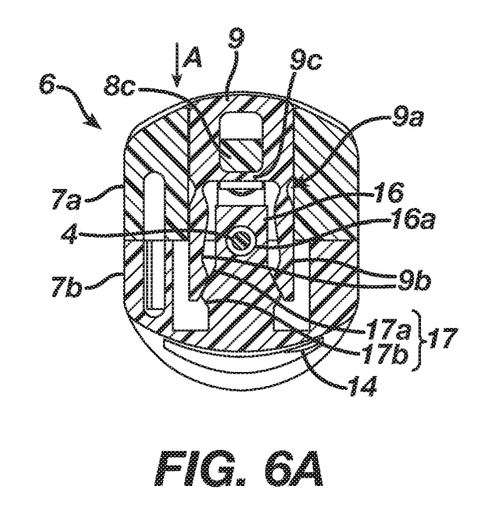
FIGS. 6A and 6B show cross-sectional views of the flip anchor cable insertion tool, along arrows 6 of FIG. 5, with the button 9 in an elevated position (FIG. 6A) and in a depressed position (FIG. 6B)

FIG. 6A shows a cross section of the inserter tool of FIG. 5, in the direction of arrows 6 of FIG. 5, where shells 7a and 7b define a housing. Button 9, shown in an elevated position, is configured to reversibly move up and down within hole 9a in upper shell 7a. A post 16 is positioned in lower shell 7b, where the post has a hole 16a. As shown in FIG. 5, hole 16a in post 16 is generally aligned with guiding tube 1, allowing cable 4, extending from guiding tube 1, to pass through hole 16a.

Figure 6B:
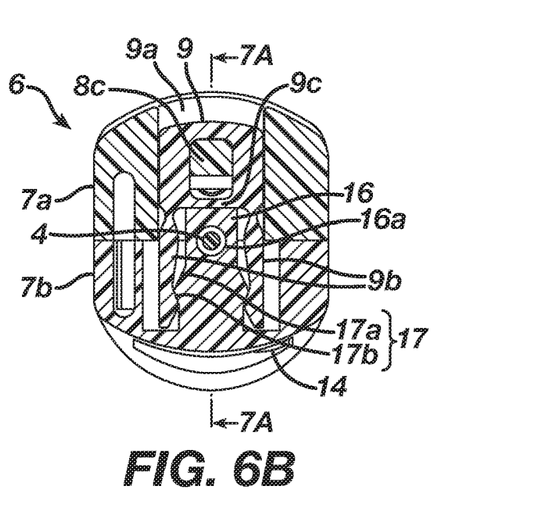

Button 9, shown in an elevated position in FIG. 6A, has a hole therethrough, with strut 9c at a lower end of the hole in button 9. Extension 8c of slider 8 extends through the hole in button 9, with hooked extension 8c engaging strut 9c of button 9. Two inwardly biased supports 9b extend downwardly from button 9. Each support 9b has a V-shaped portion, forming a trough with an outwardly flared lower end and a V-shaped opening directed toward post 16. Each side of post 16 has a V-shaped projection 17 with a sloped upper surface 17a and a sloped lower surface 17b. When button 9 is in an elevated position as shown in FIG. 6A, the outwardly flared lower end of each support 9b rests on the sloped upper surface 17a of the V-shaped projection on post 16, biasing button 9 into an elevated position. In various embodiments, the interaction between surface 17a and supports 9b causes the button 9 to enter the elevated position as shells 7a and 7b are closed about the hinge 7c. When button 9 is depressed by pushing button 9 in the direction of arrow A in FIG. 6A, the outwardly flared lower end of each support 9b slides past the sloped upper surface 17a of the V-shaped projection on post 16, as shown in FIG. 6B. The V-shaped opening on each support 9b then engages a V-shaped projection 17 on post 16, holding button 9 in a depressed position. Each support 9b may be a leaf spring or a leg. Each support 9b is biased toward an axis of button 9, but is forced away from button 9 as the outwardly flared lower end of the support 9b passes projection 17. Each support 9b moves back toward button 9 as the support engages projection 17.

As seen in FIG. 6B, when button 9 is in a depressed position, strut 9c is lowered relative to the projection 8b on slider 8. This disengages projection 8b on button 8 from button 9, allowing slider 8 to move relative to button 9.

The lower end of hook 14, visible in FIGS. 6A and 6B, holds shells 7a and 7b together in a closed position. When hook 14 is pulled toward the distal end of tool 6, against spring 14a (shown in FIG. 4), shells 7a and 7b, driven in the direction of arrows B by spring 18, shown in FIG. 4. The leaf springs 9b are pulled over the projections on post 16, disengaging the leaf springs and allowing button 9 to return to an elevated position.

Figure 7A:
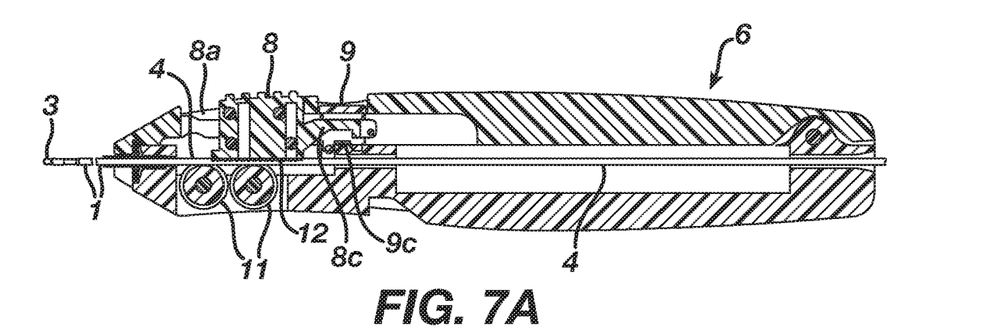
FIGS. 7A to 7C illustrate the operation of slider 8 as it moves from a clamping position to a release position.
Figure 7B:
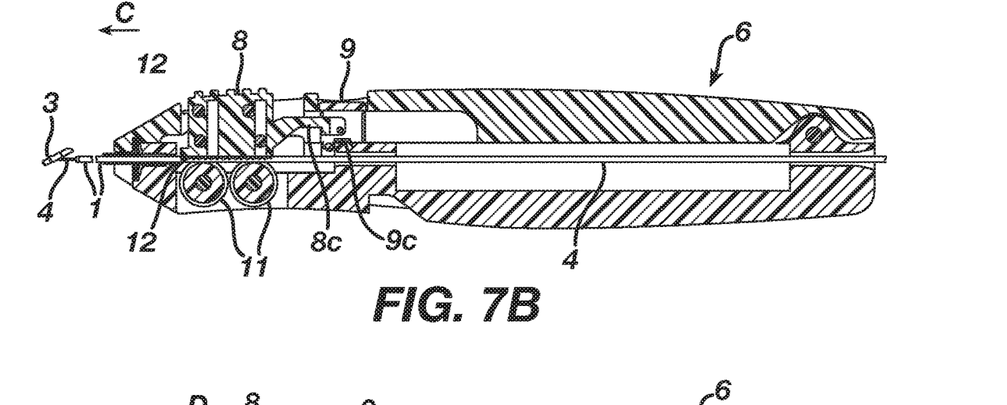

As shown in FIG. 7A, when button 9 is first depressed, strut 9c moves away from projection 8b, disengaging button 9 from slider 8. Slider 8 is still in its clamping position, so that cable 4 is clamped between low resistance surface 11 (shown as rollers in FIG. 7A) and high friction surface 12. At this point, flip anchor 3 is positioned in guiding tube 1, in a non-deployed state. When slider 8 moves distally in the direction of arrow C, as shown in FIG. 7B, the motion of the high friction surface relative to the low resistance surface drives cable 9 distally along guiding tube 1, deploying flip anchor 3 from guiding tube 1.

Figure 7C:
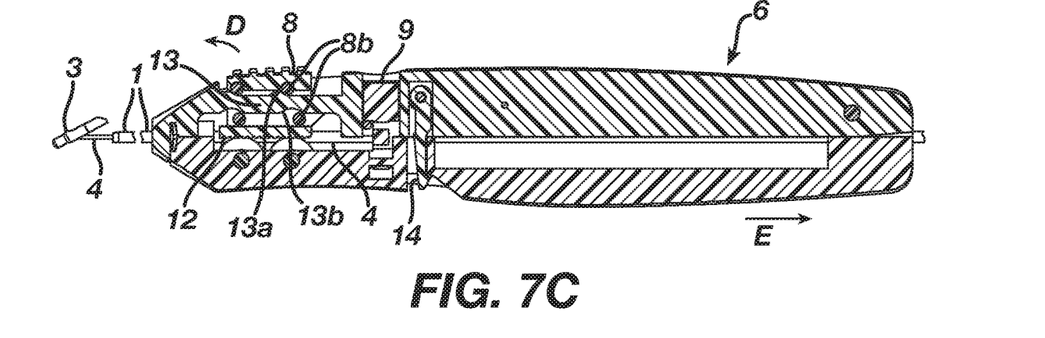

As seen in FIG. 7C, pegs 8b on the upper surface of strut 13 are adjacent to peaks 13a on the upper surface of strut 13, while pegs 8b on the lower surface of strut 13 are adjacent to troughs 13b on the lower surface of strut 13 after deployment of flip anchor 3. Further motion of slider 8 in a distal direction causes pegs 8b to move upwards along the surface of peaks 13a, while pegs 8b enter troughs 13b, causing slider 8 to move both upwardly and distally, in the direction of arrow D, relative to the low resistance surface. In this position (the release position), the low resistance and high friction surfaces are separated, releasing the clamping force on cable 4. An audible noise may be produced as the slider enters the release position. The guiding tube and tool 6 may then be pulled backwards along cable 4, in the direction of arrow E, until the cable is completely free of the guiding tube. The audible noise indicates that the tool may safely be withdrawn from the guiding tube. Also, as the slider moves along the strut 13 into the release position, its distal motion along the low resistance surface drives the flip anchor cable distally along guiding tube 1, deploying the flip anchor at the distal end of guiding tube 1. The audible noise produced as the slider enters the release position serves as an indication that the flip anchor has been deployed.

Figure 8:
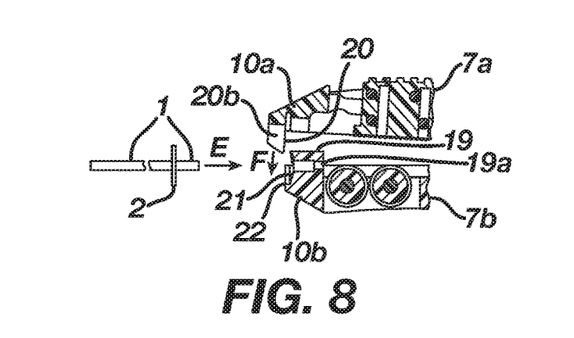
FIG. 8 illustrates positioning of the guiding tube in the flip anchor cable insertion tool of FIG. 1.
Figure 8A:
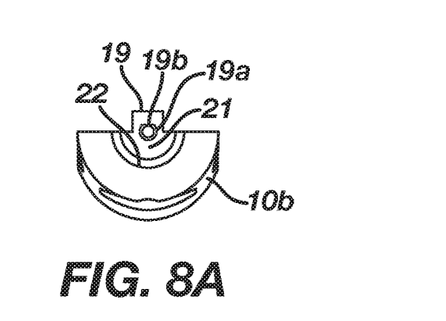
FIG. 8A illustrates a means of preventing rotation of the guiding tube.

FIG. 8 shows the positioning on the guiding tube, relative to jaws 10a and 10b. Jaw 10b includes an element 19, which may be roughly tubular or boxlike. Element 19 has a bore 19a therethrough, where the end of guiding tube 1 is inserted into bore 19a in the direction of arrow E. The bore 19a in element 19 and guiding tube 1 may each have at least one planar surface 19b to prevent undesired rotational motion of the guiding tube about its axis, as shown in the end view of shell 7b in FIG. 8A. A semicircular rim 22 on jaw 10b matches the curvature of washer 2 on guiding tube 1, and surrounds a portion of washer 2 when guiding tube 1 is positioned in the bore of element 19. The inner edge of the semicircular rim 22 and a front surface 21 of element 19 together form a first washer-engaging surface which receives a proximal side of washer 2. Jaw 10a closes over guiding tube 1, and has an inner surface 20 which faces washer 2 when jaw 10a is closed in the direction of arrow F to contact 10b, and an opening 20b which closes over guiding tube 1. Inner surface 20 forms a second washer engaging surface, which contacts a distal side of washer 2. Please note that the term "washer," as used herein, includes a disc-shaped planar structure, without being limited to a disc-shaped structure. A planar structure with a noncircular shape, such as a D shape, a teardrop shape, a polygonal shape, or an oval shape, may be considered to be washers for the purposes of this specification. A nonplanar structure, such as a conical structure with a single flat face or a biconical structure with two opposed conical faces, may also be used as washers. The shapes of the washer-engaging surfaces in the housing may be adjusted to correspond to the washer shape.

The operation of the flip anchor cable insertion tool 6 will now be described. After a user drills a hole in, for example, a bone or bones, the end of the guiding tube 1 of the device of FIG. 2 is placed in the hole until the distal end of the insertion tool passes completely through the hole in the bone. The insertion tool 6 may be rotated to a specific angular position about the axis of guiding tube 1 so that the flip anchor 3 has a desired position. At this point, button 9 is in its elevated position, and the cable is clamped with flip anchor 3 in a non-deployed state, seen in FIG. 5. Next, the user depresses the safety button 9, disengaging the safety button from slider 8. Now the user may apply a forward force on the slider 8 to drive the cable 4 in a distal direction, deploying the flip anchor, as seen in FIGS. 7A and 7B. Further distal movement releases the clamping force on cable 4, which allows the flip anchor cable 4 to be pulled out of the insertion tool 6. The cable and flip anchor may then be used to fix bones or other tissues in a desired position.

Jaws 10a and 10b of insertion tool 6 may then be opened by disengaging hook 14, and guiding tube 1 may be removed from the tool 6 and sterilized for reuse or discarded, as desired. After removal of guiding tube 1, tool 6 may be sterilized for reuse.

Figure 9A:
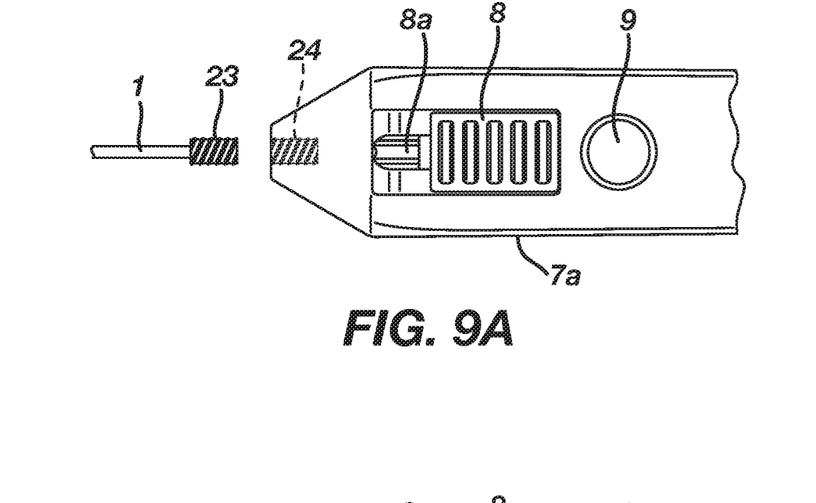
FIGS. 9A to 9C show alternative methods of positioning the guiding tube in the flip anchor cable insertion tool.
Figure 9B:
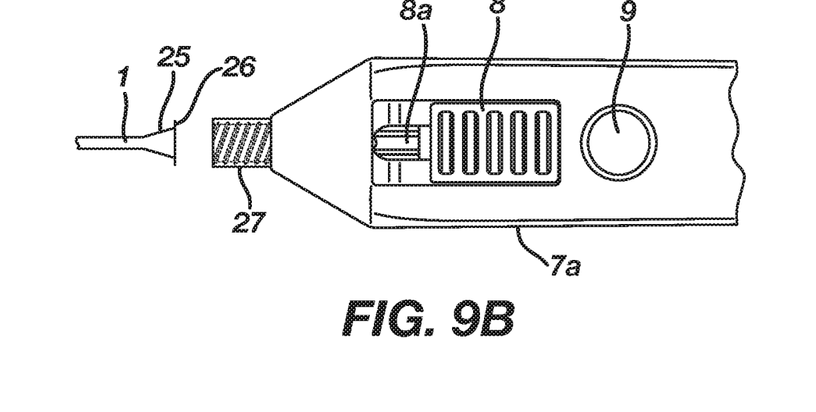
Figure 9C:
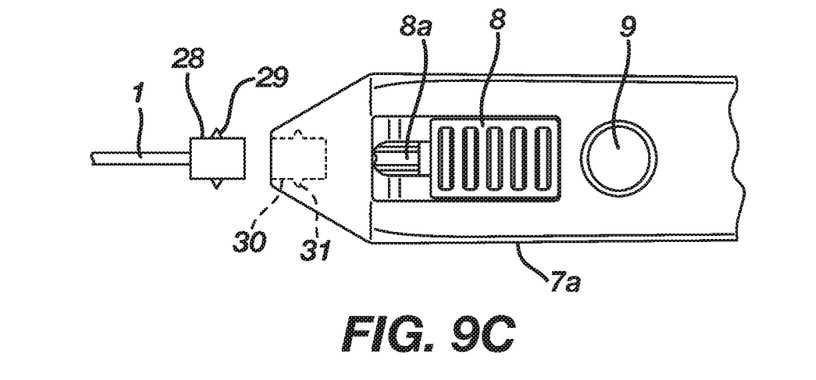

FIGS. 9A to 9C show alternative methods of attaching guiding tube 1 to a jaw of tool 6. In FIG. 9A, guiding tube 1 has a threaded male joint 23, which may be connected to a threaded female joint 24 in housing shell 7a. In FIG. 9B, the proximal end of the guiding tube has a flared end 25 with tabs 26 on an outer surface of end 25. Tabs 26 screw into a sleeve 27 with a threaded inner surface, where the sleeve surrounds an opening in housing shell 7a. In FIG. 9C, the proximal end of the guiding tube 1 has a male joint 28 with a ridge 29 thereon, and housing shell 7a has a corresponding female joint 30 with a groove 31. Guiding tube 1 and shell 7a may be connected by fitting male joint 28 into female joint 30 until ridge 29 releasably engages groove 31, in a "snap-fit" type connection.

Figure 10:
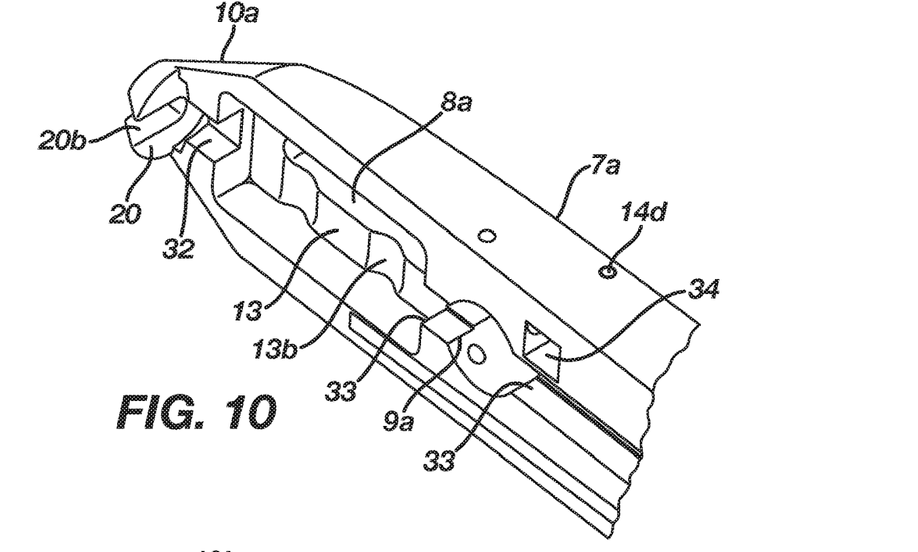
FIG. 10 shows a view of the internal structure of an upper housing of the flip anchor cable insertion tool of FIG. 1.

FIG. 10 shows an interior view of the upper shell 7a of insertion tool 6. The slot 8a for slider 8 and the hole 9a for button 9 are shown. One of struts 13 can be seen, along with troughs 13b. As discussed above, pegs on slider 9 ride along struts 13, and enter troughs 13b as the slider moves distally along tool 6. Opening 34 is provided for hook 14, while pin 14d holds hook 14 rotatably in opening 34. Jaw 10a at the distal end of shell 7a includes an opening 20b configured to fit over guiding tube 1, adjacent to washer 2. Jaw 10a has an inner surface 20 configured to face a surface of washer 2.

Openings 32 and 33 are configured to receive structural elements from lower shell 7b of tool 6.

Figure 11:
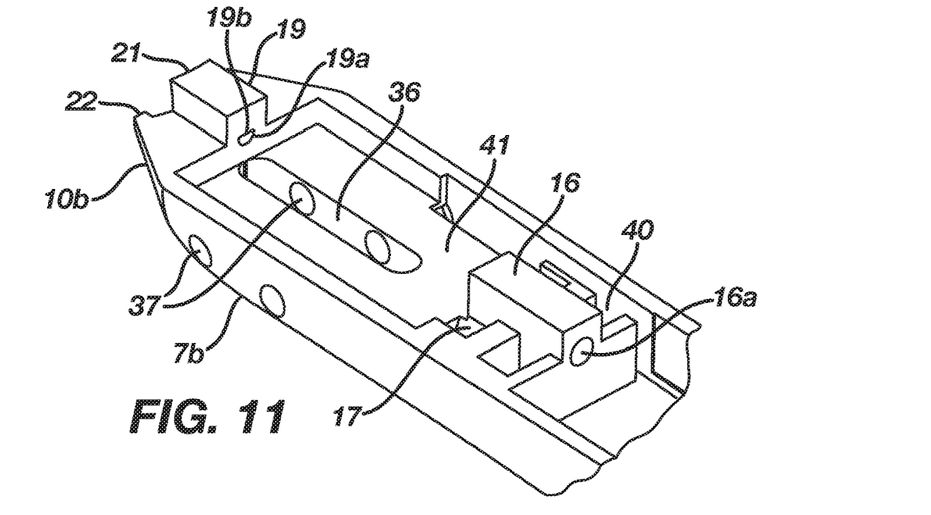
FIG. 11 shows a view of the internal structure of a lower housing of the flip anchor cable insertion tool of FIG. 1.
Figure 12:
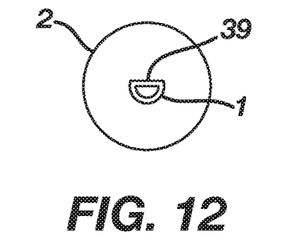
FIGS. 12 and 13 show embodiments of a guiding tube for a flip anchor insertion cable, configured to engage with the lower housing of a flip anchor cable insertion tool.

FIG. 11 shows an interior view of the lower shell 7b of insertion tool 6. Post 16 has projections 17, discussed above, thereon. The upper surface of post 16 fits into openings 33 in upper shell 7a. Element 19 has a bore 19a therethrough, and is positioned so that the upper surface of element 19 fits into opening 32 in upper shell 7a. Jaw 10b at the distal end of shell 7b includes a rim 22, configured to fit around a peripheral edge of washer 2, attached to guiding tube 1. An outer surface 21 of element 19 is configured to fit against a surface of washer 2, with a proximal end of guiding tube 1 fitting into bore 19a. When jaws 10a and 10b are secured together, washer 2 is held between surface 21 of lower shell 7b and surface 20 of upper shell 7a, securing guiding tube in position. As seen in FIG. 12, guiding tube 1 passes through washer 2. If desired, guiding tube 1 may have at least one planar surface 39. As seen in FIG. 12, bore 19a may be constructed with a corresponding planar surface 38. When the guiding tube is inserted into bore 19a, surfaces 38 and 39 interact to prevent undesired rotation of the guiding tube, relative to tool 6, so that tool 6 and guiding tube 1 have a fixed relative orientation. Hole 16a in post 16 is configured to allow a flip anchor cable extending from guiding tube 1 to pass therethrough. In certain embodiments, slot 36 receives rollers, while holes 37 are configured to hold axles supporting the rollers, so that the rollers are rotatably mounted in slot 36 as a low resistance surface. In other embodiments, slot 36 and holes 37 may be absent from shell 7b, and replaced by a planar low friction surface 41, configured to face high friction surface 12 on slider 8, shown in FIG. 7A. Opening 40 corresponds to opening 34 in upper shell 7a, and receives hook 14.

Figure 13:
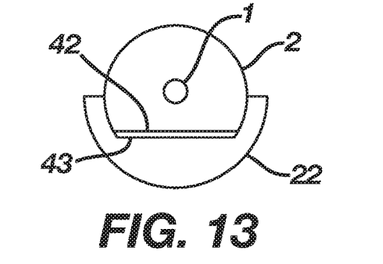

FIG. 13 shows an alternative method of preventing rotation between the insertion tool 6 and the guiding tube 1. As seen in FIG. 13, guiding tube 1 passes through washer 2. Guiding tube 1 has a circular cross section. However, washer 2 has a peripheral edge with at least one planar surface 42. Rim 22 of lower shell 7b has an inner edge with a corresponding planar surface 43. When the guiding tube is inserted into bore 19a, surfaces 42 and 43 interact to prevent undesired rotation of the guiding tube, relative to tool 6.

It should be appreciated by those skilled in the art that any diagrams or schematic drawings herein represent conceptual views of illustrative structures embodying the principles of the invention.

Although the various embodiments have been described in detail with reference to certain aspects thereof, it should be understood that the invention is capable of other embodiments and its details are capable of modifications in various obvious respects. As is readily apparent to those skilled in the art, variations and modifications can be affected while remaining within the spirit and scope of the invention. Further, various elements from the various embodiments may be combined to form other embodiments that are within the spirit and scope of the invention. Accordingly, the foregoing disclosure, description, and figures are for illustrative purposes only and do not in any way limit the invention, which is defined only by the claims.

What is claimed is:

1. A system for use in deploying a flip anchor cable, wherein said flip anchor cable comprises a flip anchor, and a cable connected to the flip anchor, said system comprising:
a housing, the housing having a first end and a second end;
a guiding tube having a first axis and a bore therethrough, said guiding tube having a proximal end releasably connected to the first end of said housing and a distal end configured to hold said flip anchor;
a mechanism on said housing, said mechanism having:
a low resistance surface;
a slider on said housing, said slider having a high friction surface facing said low resistance surface, said slider being configured to move between a clamping position configured to clamp the cable between said low resistance surface and said high friction surface and a release position configured to allow the cable to move freely on said low resistance surface; and
a safety button on said housing, said safety button being configured to move between an elevated position where the safety button holds the slider in said clamping position, and a depressed position where the safety button releases the slider, allowing it to enter the release position,
wherein the slider is configured to move the cable distally upon movement from said clamping position to said release position, deploying said flip anchor.

2. The system of claim 1, wherein the low resistance surface comprises a low friction surface, and the high friction surface is a toothed surface, an etched surface, a sandblasted surface, or a surface coated with a layer of an aggregate and a binder.

3. The system of claim 1, wherein the low friction surface comprises a low friction polymer selected from the group consisting of polytetrafluoroethylene, polyimide, PEEK, polyphenylene sulfide, nylon, silicones, polyacetals, and polyesters.

4. The system of claim 1, wherein the low resistance surface comprises a roller, and the high friction surface is a toothed surface.

5. The system of claim 1, wherein the low resistance surface comprises at least two rollers, and the high friction surface is a toothed surface.

6. The system of claim 1, wherein:
the safety button is configured to be biased toward the elevated position and configured to be releasably locked into said depressed position; and
the slider is configured to be biased toward the safety button and configured to engage the safety button when the safety button is in said elevated position.

7. The system of claim 6, wherein:
the slider is configured to disengage the safety button when the safety button is in said depressed position.

8. The system of claim 1, wherein:
the guiding tube is disposable; and
the proximal end of the guiding tube fits into an opening in the housing.

9. The system of claim 8, wherein the housing is reusable.

10. The system of claim 8, wherein the proximal end of the guiding tube has a washer thereon, wherein the opening in the housing has a surface configured to engage said washer and a bore configured to receive said guiding tube, wherein said guiding tube has an outer surface with a planar portion and said bore has an inner surface with a planar portion, and wherein the outer surface of the guiding tube and the inner surface of the bore interact to prevent rotation of the guiding tube.

11. The system of claim 8, wherein the proximal end of the guiding tube is a threaded end, which fits into the opening in said housing, said opening in said housing being threaded.

12. The system of claim 8, wherein the proximal end of the guiding tube has tabs on an outer surface, said tabs screwing into a sleeve with a threaded inner surface, said sleeve surrounding said opening in said housing.

13. The system of claim 8, wherein the proximal end of the guiding tube has a ridge, and the opening in said housing has a groove;

wherein said ridge releasably engages said groove.

14. The system of claim 8, wherein:

the proximal end of the guiding tube has a washer;

the second end of said housing comprises a hinge, said hinge allowing said housing to be divided into a first half and a second half, said first half and said second half each comprising a washer-engaging surface, wherein one of said first half and said second half comprises the opening; and said washer-engaging surfaces in said first half and said second half are configured to lock the washer of the guiding tube to said housing when said hinge is closed, and release the washer when said hinge is open.

15. The system of claim 14, wherein the proximal end of the guiding tube has an outer surface with a planar portion and the opening has an inner surface with a planar portion, wherein the outer surface of the guiding tube and the inner surface of the opening in the housing interact to prevent rotation of the guiding tube.

16. The apparatus of claim 1, wherein the system is configured to produce an audible noise when the slider enters the release position, indicating that the flip anchor has been deployed.

17. A system for use in deploying a flip anchor cable, wherein said flip anchor cable comprises a flip anchor, and a cable connected to the flip anchor, said system comprising:

a housing, the housing having a first end having an opening and a second end, the second end of said housing comprising a hinge, said hinge allowing said housing to be divided into a first half and a second half;

a guiding tube having a first axis and a bore therethrough, said guiding tube having a proximal end, said proximal end being releasably mounted in said opening in the first end of the housing, and a distal end configured to hold said flip anchor;

a mechanism having a low resistance surface and a slider on the housing, said slider having a high friction surface facing said low resistance surface, said slider being configured to move between a clamping position configured to clamp the cable between said low resistance surface and said high friction surface; and a release position configured to allow the cable to move freely on said low resistance surface; and a safety button on the first half of the housing, said safety button being configured to move between an elevated position where the safety button holds the slider in said clamping position, and a depressed position where the safety button releases the slider, allowing it to enter the release position, wherein the slider is configured to move the cable distally upon movement from said clamping position to said release position, deploying said flip anchor, and wherein the safety button is configured to engage the second half of the housing upon movement into the depressed position, locking the safety button in the depressed position until the hinge is opened.

18. A tool for use in deploying a flip anchor cable from a guiding tube having a bore therethrough, wherein said flip anchor cable comprises a flip anchor deployably positioned in said guiding tube, and a cable connected to the flip anchor, said tool comprising:

a housing, the housing having a first end configured to receive the guiding tube and a second end;

a mechanism having a low resistance surface and a slider on said housing, said slider having a high friction surface facing said low resistance surface, said slider being configured to move between a clamping position configured to clamp the cable connected to the flip anchor between said low resistance surface and said high friction surface; and a release position configured to allow the cable connected to the flip anchor to move freely on said low resistance surface; and a safety button on said housing, said safety button being configured to move between an elevated position where the safety button holds the slider in said clamping position, and a depressed position where the safety button releases the slider, allowing it to enter the release position, wherein the slider is configured to move the cable connected to the flip anchor distally upon movement from said clamping position to said release position, deploying said flip anchor from said guiding tube.

19. A system for use in positioning a flip anchor, said system comprising:

a flip anchor cable comprising a flip anchor, and a cable connected to the flip anchor;

a housing holding a first portion of the cable connected to the flip anchor, the housing having a first end and a second end;

a guiding tube having a proximal end releasably connected to the first end of said housing and a distal end, said guiding tube being held in a fixed orientation relative to the housing, wherein a second portion of the cable passes through a bore of the guiding tube so that the flip anchor is positioned at the distal end of the guiding tube, in a fixed orientation relative to the guiding tube;

a mechanism having a low resistance surface and a slider on said housing, said slider having a high friction surface facing said low resistance surface, said slider being configured to move between a) a clamping position configured to clamp the first portion of the cable between said low resistance surface and said high friction surface; and b) a release position configured to allow the first portion of the cable to move freely on said low resistance surface; and a safety button on said housing, said safety button being configured to move between a clamping position where the safety button holds the slider in said first position, and a depressed position where the safety button releases the slider, allowing it to enter the release position, wherein the slider drives the cable distally through said guiding tube upon movement from said clamping position to said release position, deploying said flip anchor.

20. The system of claim 19, wherein:

the proximal end of the guiding tube has an outer surface with a planar portion and the first end of the housing has an opening configured to receive said guiding tube, the opening in the housing having an inner surface with a corresponding planar portion, the outer surface of the guiding tube and the inner surface of the opening in the housing interact to prevent rotation of the guiding tube; and the distal end of the guiding tube has an inner surface which is configured to prevent rotation of the flip anchor around an axis of the guiding tube.

21. The apparatus of claim 19, wherein the system is configured to produce an audible noise when the slider enters the release position, indicating that the flip anchor has been deployed.

* * * * *